US009804076B2

(12) United States Patent
Harrell et al.

(10) Patent No.: US 9,804,076 B2
(45) Date of Patent: Oct. 31, 2017

(54) USE OF DETECTION TECHNIQUES FOR CONTAMINANT AND CORROSION CONTROL IN INDUSTRIAL PROCESSES

(71) Applicant: Baker Hughes Incorporated, Houston, TX (US)

(72) Inventors: Bradley G. Harrell, Pearland, TX (US); Sai Reddy Pinappu, Houston, TX (US); George G. Duggan, Katy, TX (US)

(73) Assignee: Baker Hughes, a GE company, LLC, Houston, TX (US)

( * ) Notice: Subject to any disclaimer, the term of this patent is extended or adjusted under 35 U.S.C. 154(b) by 324 days.

(21) Appl. No.: 14/204,301

(22) Filed: Mar. 11, 2014

(65) Prior Publication Data

US 2014/0260708 A1    Sep. 18, 2014

Related U.S. Application Data

(60) Provisional application No. 61/779,470, filed on Mar. 13, 2013.

(51) Int. Cl.
*G01N 17/00* (2006.01)
*G01N 33/28* (2006.01)

(52) U.S. Cl.
CPC ......... *G01N 17/00* (2013.01); *G01N 33/2823* (2013.01)

(58) Field of Classification Search
CPC .................................................. G01N 17/00
See application file for complete search history.

(56) References Cited

U.S. PATENT DOCUMENTS

| | | | |
|---|---|---|---|
| 6,194,900 B1 | 2/2001 | Freeman | |
| 8,070,956 B2 | 12/2011 | Peterman | |
| 8,414,755 B2 | 4/2013 | Peterman | |
| 8,702,976 B2 | 4/2014 | Peterman | |
| 2004/0045350 A1* | 3/2004 | Jones | E21B 43/38 73/152.23 |
| 2005/0051719 A1 | 3/2005 | Miller et al. | |
| 2007/0181798 A1* | 8/2007 | Lubkowitz | G01N 30/8675 250/288 |
| 2008/0102529 A1 | 5/2008 | Butler et al. | |
| 2010/0118301 A1 | 5/2010 | Vondras et al. | |
| 2010/0136699 A1* | 6/2010 | Drese | B01L 3/5027 436/43 |
| 2010/0175467 A1* | 7/2010 | DiFoggio | E21B 49/087 73/152.28 |
| 2011/0139464 A1* | 6/2011 | Henderson | E21B 21/01 166/370 |
| 2013/0137128 A1* | 5/2013 | MacKay | G01N 21/76 435/26 |
| 2014/0369889 A1* | 12/2014 | Mostowfi | G01N 33/2823 422/82.09 |
| 2017/0074799 A1 | 3/2017 | Peterman et al. | |

FOREIGN PATENT DOCUMENTS

WO    2012058619 A1    5/2012

OTHER PUBLICATIONS

Gough, M. A., et al. "Molecular Monitoring of Residual Corrosion Inhibitor Actives in Oilfield Fluids: Implication for Inhibitor Performance", 1998, Corrosion 98, Paper No. 33.*
Talzi, V.P., "NMR Determination of the Total Composition of Commerical Absorbents Based on Monoethanolamine", Russian Journal of Applied Chemistry, vol. 7 No. 3, 2004.*
"Sensitivity in NMR" Oct. 26, 2009, https://www.chem.wisc.edu/~cic/nmr/Guides/Other/sensitivity-NMR.pdf.*
Bord, N., Crétier, G., Rocca, J.L., Bailly, C., Souchez, J.P., "Determination of diethanolamine or N-methyldiethanolamine in high ammonium concentration matrices by capillary electrophoresis with indirect UV detection: application to the analysis of refinery process waters", Analytical and bioanalytical chemistry, 2004, 380(2); abstract only.
Fekete, A., Frommberger, M., Ping, G., Lahaniatis, M.R., Lintelman, J., Fekete, J., Gebefugi, I., Malik, A.K., Kettrup, A., Schmitt-Kopplin, P., "Development of a capillary electrophoretic method for the analysis of low-molecular-weight amines from metal working fluid aerosols and ambient air", Electrophoresis, 2006, 27(5-6), 1237-1247; abstract only.
Urbanek, Marek; Delaunay, Nathalie; Michel, Regis; Varenne, Anne; Gareil, Pierre; "Analysis of sub-ppb levels of Fe (II), Co(II), and Ni(II) by electrokinetic supercharging preconcentration, CZE separation, and in-capillary derivatization", Electrophoresis (2007), 28(20, ; abstract only.
Kokkonen, Raimo; Siren, Heli; Kauliomaeki, Seppo; Rovio, Stella; Luomanpera, Kaija; "On-line process monitoring of water-soluble ions in pulp and paper machine waters by capillary electrophoresis", Journal of Chromatography, A (2004), 1032(1-2), 243-252.
Chen, C., Hahn, J.H., "Enhanced aminophenols monitoring using in-channel amperometric detection with dual-channel microchip capillary electrophoresis", Environmental Chemistry Letters, 2011, 9(4); abstract only.

(Continued)

*Primary Examiner* — Paul West
(74) *Attorney, Agent, or Firm* — Mossman, Kumar & Tyler, P.C.

(57) ABSTRACT

Industrial fluids may be monitored at the site of each industrial fluid by introducing a sample of the industrial fluid into a device employing a detection technique for detecting at least one composition within the sample. The detection technique may be or include surface enhanced Raman scattering (SERS), mass spectrometry (MS), nuclear magnetic resonance (NMR), ultraviolet light (UV) spectroscopy, UV spectrophotometry, indirect UV spectroscopy, contactless conductivity, laser induced fluorescence, and combinations thereof. In one non-limiting embodiment, a separation technique may be applied to the sample prior to the introduction of the sample into the device for detecting the composition.

16 Claims, No Drawings

(56) References Cited

OTHER PUBLICATIONS

Frattini, Paul et al., "Improving Ion Identification," Nuclear Engr Int'l 54 (658), 4 pp. (2009).
Shackman, Jonathan et al., "GEMBE for High Throughput Multiplexed Microfluidic Devices," Analytical Chemistry, vol. 79, pp. 565-571 (2007).
Topguard Overhead Corrosion Control Brochures, 4 pp. (2013).
Loos, Robert et al., "LC-MS-MS Analysis and Occurrence of Octyl- and Nonylphenol, Their Ethoxylates and Their Carboxylates in Belgian and Italian Textile Industry, Waste Water Treatment Plant Effluents and Surface Waters," Chemosphere, vol. 66, No. 4, pp. 690-699 (2007).
Campo, Pablo et al., "A Liquid Chromatography-Electrospray Ionization-Tandem Mass Spectrometry Study of Ethanolamines in High Salinity Industrial Wastewaters," Talanta, vol. 80, No. 3, pp. 110-1115 (2010).
Harynuk, James J. et al., "Study of Alkyl Phosphates in Industrial Petroleum Mixtures by Comprehensive Two-Dimensional Gas Chromatography Time-of-Flight Mass Spectrometry," Analytical and Bioanalytical Chemistry, vol. 401, No. 8, pp. 2415-2422 (2011).
International Search Report and Written Opinion in PCT/US2014/24539, dated Jul. 28, 2014.

\* cited by examiner

USE OF DETECTION TECHNIQUES FOR CONTAMINANT AND CORROSION CONTROL IN INDUSTRIAL PROCESSES

CROSS-REFERENCE TO RELATED APPLICATION

This application claims the benefit of Provisional Patent Application No. 61/779,470 filed Mar. 13, 2013, which is incorporated by reference herein in its entirety.

TECHNICAL FIELD

The present invention relates to monitoring at least one industrial fluid at the site of the industrial fluid by introducing a sample of the industrial fluid into a device and detecting at least one composition in the fluid.

BACKGROUND

It is often desirable to monitor industrial fluids, such as a refinery fluid, a production fluid, refinery feedstock, combinations thereof, and/or derivatives thereof, but it has been particularly troublesome to monitor industrial fluids in a timely manner. Typically, a sample of the industrial fluid is collected at the site of the industrial fluid, but the sample is then sent to a remote location for analyzing any compositions therein. Such analytical techniques include, but are not limited to separation techniques, detection techniques, and the like. Once the results are received, the parameters related to the industrial fluid may be altered accordingly. Examples of such parameters include temperature, pH, velocity, and the like. Conditions affecting the fluid may also include the amount of fuel additives therein, such as hydrogen sulfide scavengers or other types of contaminant removal technology, neutralizers, demulsifiers, and the like.

There are many different types of detection techniques for detecting compositions within a fluid, such as surface enhanced Raman spectroscopy (SERS) (often called surface enhanced Raman scattering), which is a surface-sensitive detection technique that may be used to detect compositions adsorbed on rough metal surfaces or nanostructured surfaces.

Mass spectrometry (MS) displaying the spectra of the mass(es) for at least one molecule within a sample of material. It determines the elemental composition of a sample, the masses of compounds and of molecules, and it may elucidate the chemical structures of molecules. Mass spectrometry works by ionizing chemical compounds to generate charged molecules or molecule fragments and measuring their mass-to-charge ratios. In a typical MS procedure, a sample is ionized and the ions separate according to their mass-to-charge ratio. The signal generated from the detected ions forms a spectra where the spectra indicates the mass(es) of each compound or molecule based on known masses for a given spectra.

Nuclear magnetic resonance (NMR) spectroscopy determines the physical and chemical properties of atoms or the molecules in which they are contained by exploiting the magnetic properties of certain atomic nuclei. The analyte absorbs electromagnetic radiation at a frequency that is characteristic of the isotope. The resonant frequency, energy of the absorption, and the intensity of the signal are proportional to the strength of the magnetic field. The generated spectrum provides detailed information about the structure, dynamics, reaction state, and chemical environment of molecules.

Ultraviolet visible spectroscopy or ultraviolet visible spectrophotometry utilizes absorption spectroscopy or reflectance spectroscopy in the ultraviolet-visible spectral region. This technique uses wavelengths of light in the visible and adjacent (near-UV and near-infrared (NIR)) ranges. Typically, the eluent includes an ion-pair reversed-phase system with a UV-absorbing ion, since absorption measures transitions from the ground state to the excited state. The UV spectroscopy or spectrophotometry detects or identifies the composition that absorbs UV light.

Indirect UV spectrometry allows non-ionic substances with low or no UV-absorptive properties to be detected and quantified. The mobile phase may have an uncharged component with high UV-absorbance. Polar or non-polar bonded stationary phases may be used, depending on the hydrophobic character of the analytes. Indirect UV detection may be used in applications where the composition within the sample may be or include, but not limited to organic solvents, carbohydrates, polyols, halide ions, amines, and the like.

Capacitively-coupled contactless conductivity detection (C4D) systems apply a high voltage AC waveform to a transmitter electrode adjacent to a tube or channel in which electrophoretic, electroosmotic, or chromatographic flow is occurring. As analyte ions pass into the detection region, they cause small changes to the overall sample conductivity. Continuous monitoring of the conductivity signal will show a series of peaks, the areas (or heights) of which are related to analyte concentration. The signal is processed like a conventional chromatogram. The C4D electrodes do not make direct contact with the sample. Thus, they are electrically isolated from the sample (ideal for electrophoresis detection), and electrode fouling is eliminated. Most analytes for a C4D system are ionic. Sensitivity is typically similar to UV-visible absorption detection.

Laser-induced fluorescence or LED induced fluorescence is another spectroscopic method. The composition may be examined by exciting the composition with a laser. The wavelength of the laser is one at which the composition has the largest cross-section. The composition will become excited and then de-excite (or relax) and emit light at a wavelength longer than the excitation wavelength.

'Detection' is defined herein as a method of confirming the presence of a composition or analyte in a fluid; whereas, 'quantitation' is defined herein as a method of determining the concentration of an analyte in a fluid. While detection techniques may be combined with quantitation techniques in a particular device, each technique may also be performed separately.

There are also many types of separation techniques, which include gas chromatography, ion-exchange chromatography, high performance liquid chromatography, electrokinetic chromatography (EKC), capillary isotachophoresis (CITP), capillary isoelectric focusing (CIEF), and electrophoresis, such as affinity capillary electrophoresis (ACE), non-aqueous capillary electrophoresis (NACE). Chromatography typically involves a mobile phase, a stationary phase, and an analyte; although, CEC utilizes a pseudostationary phase instead of a mobile phase.

The solution having the composition of interest is usually called a sample, and the individually separated components are called analytes. The analyte used for chromatographic purposes may have at least one composition of interest that is dissolved in a fluid, which is the mobile phase. The mobile phase carries the analyte through a structure that has a stationary phase therein. The various compositions of the analyte travel at different speeds, and the compositions separate based on differential partitioning between the mobile phase and the stationary phase. Subtle differences in a compound's partition coefficient change the rate of retention based on the type of stationary phase.

In traditional electrophoresis, electrically charged analytes move in a conductive liquid medium under the influence of an electric field. The species of compositions within a sample may be separated based on their size to charge ratio in the interior of a small capillary filled with an electrolyte. Conducting these separations in small fused silica capillaries or microchannels (10-100 μm internal diameter) allows for high voltages (up to 30 kV) to be applied, extremely small sample volume (0.1-10 μL) for the analyte, rapid separation times (minutes), and/or high resolving power (hundreds of thousands of theoretical plates). Electrophoresis may be combined with chromatographic techniques based on the type of analysis desired.

Gas chromatography (GC) separates and analyzes compounds that may be vaporized without decomposition. The mobile phase is a carrier gas, such as an inert or unreactive gas. The stationary phase may be a microscopic layer of liquid or polymer on an inert solid support inside a column, such as a piece of glass or metal tubing. Ion chromatography (or ion-exchange chromatography) separates ions and polar molecules within an analyte based on the charge of the molecules.

High-performance liquid chromatography (sometimes referred to as high-pressure liquid chromatography), HPLC, separates analytes by passing them, under high pressure, through a column filled with a stationary phase. The interactions between the analytes and the stationary phase and mobile phase lead to the separation of the analytes.

Capillary electrophoresis (CE), also known as capillary zone electrophoresis (CZE), can be used to separate ionic species by their charge and frictional forces and hydrodynamic radius similar to the generic electrophoresis technique discussed above. CE is simple to use, operates at a high speed, and requires small amounts of sample or reagents.

Gradient elution moving boundary electrophoresis (GEMBE) allows for electrophoretic separations in short (1-3 cm) capillaries or microchannels. With GEMBE, the electrophoretic migration of analytes is opposed by a bulk counterflow of separation buffer through a separation channel. The counterflow velocity varies over the course of a separation so that analytes with different electrophoretic mobilities enter the separation channel at different times and are detected as 'moving boundary', stepwise increases, in the detector response. The resolution of a GEMBE separation may be dependent on the rate at which the counterflow velocity is varied (rather than the length of the separation channel), and relatively high-resolution separations may be performed with short microfluidic channels or capillaries.

Capillary electrochromatography (CEC) utilizes electro osmosis to drive the mobile phase through the chromatographic bed. CEC combines two analytical techniques, i.e. HPLC and CE. In CEC, capillaries packed with an HPLC stationary phase, are subjected to a high voltage. Separation is achieved by electrophoretic migration of solutes and differential partitioning.

These types of separations and detection techniques have not been useful for detecting compositions within industrial fluids at the site of at least one industrial fluid. More so, the process of sending a sample to a remote location for performing a separation technique and/or detecting a composition often takes several days or weeks. Thus, it would be desirable to develop a method for detecting compositions within the industrial fluid at the site of the industrial fluid in a relatively short amount of time, e.g. five hours or less.

SUMMARY

There is provided, in one form, a method for monitoring at least one industrial fluid by introducing a sample into a device employing a detection technique for detecting at least one composition within the sample. The detection technique may be or include surface enhanced Raman scattering (SERS), mass spectrometry (MS), nuclear magnetic resonance (NMR), ultraviolet light (UV) spectroscopy, UV spectrophotometry, indirect UV spectroscopy, contactless conductivity, laser induced fluorescence, and combinations thereof. The industrial fluid may be or include a refinery fluid, a production fluid, cooling water, process water, drilling fluids, completion fluids, production fluids, crude oil, feed streams to desalting units, outflow from desalting units, refinery heat transfer fluids, gas scrubber fluids, refinery unit feed streams, refinery intermediate streams, finished product streams, and combinations thereof. The method may occur in an amount of time that is less than about 24 hours.

In another non-limiting embodiment, a separation technique may be performed on the sample of the industrial fluid prior to the introduction of the fluid into the device. The separation technique may be or include capillary electrochromatography (CEC); electrokinetic chromatography (EKC), such as capillary electrokinetic chromatography (CEC), micellar electrokinetic capillary chromatography (MECC), micellar electrokinetic chromatography (MEKC), ion exchange electrokinetic chromatography (IEEC); capillary isotachophoresis (CITP); capillary isoelectric focusing (CIEF), and electrophoresis, such as affinity capillary electrophoresis (ACE), non-aqueous capillary electrophoresis (NACE), capillary electrophoresis (CE), capillary zone electrophoresis (CZE), gradient elution moving boundary electrophoresis (GEMBE); and combinations thereof. After the sample has been introduced to the device, at least one composition may be detected, such as but not limited to amines, sulfides, chlorides (organic and inorganic), bromides, organic acids, perchlorates, selenates, phosphates, polyphosphates, cyanide, selenium, borate, mercaptans; primary amines, secondary amines, and tertiary amines, methylamine (MA), ethanolamine (MEA), dimethylethanolamine (DMEA), ammonia; mercaptoethanol, thioglycolic acid, glycols, polyols, polydimethylsiloxanes, organic halides, $C_1$-$C_{22}$ organic acids, hydroxyacids, imidazoline, alkyl pyridine quaternary compounds, imides, amides, thiophosphate esters, phosphate esters, polyamines, dimethyl fatty amines, quaternized dimethyl fatty amines, ethylene vinylacetate, phenylenediamine (PDA), hindered phenols, nitrites, sulfites, N,N'-diethyl hydroxylamine, hydrazine, ascorbic acid, organic nitroxides, triazoles and polytriazoles, hydroxylamines, acrylic acids and sulfonic acids, fatty acid methyl ester (FAME), propargyl alcohols, acetylenic alcohols, pyroles, indoles, indenes, thiophenols, dyes, $H_2S$; MEA triazine (also known as 2,2',2''-(1,3,5-triazinane-1,3,5-triyl)triethanol, or 1,3,5-tris(2-hydroxyethyl)hexahydro-s-triazine, or tris-hydroxyethyl-hexahydro-triazine, or HHTT); MEA thiadiazine (also known as 2,2'-(1,3,5-thiadiazinane-3,5-diyl)diethanol), MEA dithiazine (also known as 2-(1,3,5-dithiazinan-5-yl)ethanol), MA triazine (also known as 1,3,5-trimethyl-1,3,5-triazinane), MA thiadiazine (also known as 3,5-dimethyl-1,3,5-thiadiazinane); MA dithiazine (also known as 5-methyl-1,3,5-dithiazinane), metal ions; polynuclear aromatic hydrocarbons; benzene; toluene; xylene; ethylbenzene; and combinations thereof. Alternatively, the type of chemical detected may be or include, but is not limited to, scale inhibitors, hydrogen sulfide scavengers, mercaptan scavengers, antifoam additives, antifoulant additives, paraffin control additives, cleaners/degreasers, lubricity additives, cold flow additives, oxygen scavengers, neutralizers, detergents, hydrogen sulfide scavengers, mercaptan scavengers, corrosion inhibitors, neutralizers, detergents, demulsifiers, derivatives thereof, or degradation products and combinations thereof.

There is provided, in another form, a fluid composition having a conditioned sample of an industrial fluid prepared for analysis by a device employing a detection technique, such as surface enhanced Raman scattering (SERS), mass spectrometry (MS), nuclear magnetic resonance (NMR), ultraviolet light (UV) spectroscopy, UV spectrophotometry, indirect UV spectroscopy, contactless conductivity, laser induced fluorescence, and combinations thereof. The industrial fluid may be or include a refinery fluid, a production fluid, cooling water, process water, drilling fluids, completion fluids, production fluids, crude oil, feed streams to desalting units, outflow from desalting units, refinery heat transfer fluids, gas scrubber fluids, refinery unit feed streams, refinery intermediate streams, finished product streams, and combinations thereof. The conditioned sample is compositionally distinct as compared to a non-conditioned sample of the industrial fluid.

Detecting compositions within an industrial fluid at the sight of the industrial fluid may allow for better monitoring of the industrial fluids in real-time.

DETAILED DESCRIPTION

Recent advances in separation techniques and/or detection techniques have made many chemical analyses much more rapid and efficient. These advances (e.g. miniaturization, reduced power consumption, portability, etc.) have impacted both the physical/operational characteristics of the separations and/or detectors of the devices used for such techniques, as well as the technical capabilities, such as theoretical plates, high resolving power, rapid separation, and the like. Additionally, detectors have become much more sensitive and are capable of detecting compositions in trace amounts. Some, such as SERS, even approach single molecule detection under ideal conditions, i.e. a laboratory-made sample with few or no interfering analytes.

These advances have led to powerful miniaturized machines that may be operated at the site of industrial fluids for detecting compositions within the fluid and/or monitoring the parameters of the fluid. In one non-limiting example, the data obtained would be valuable for predicting corrosion or fouling risk (when used in combination with modeling), actuating or activating chemical treatment programs, or optimizing process variables to eliminate deleterious conditions.

In another non-limiting embodiment, at least one sample may be taken from an industrial fluid; analyzed on-site for particular compositions in a short period of time by a detection technique; and the data passed to a modeling program (CRM), operator, or chemical pump (e.g. one delivering a contaminant removal additive) in order to alter a parameter of the fluid or inject an additive to avoid or mitigate conditions that could damage process equipment or reduce unit throughput. CRM refers to the TOPGUARD™ Corrosion Risk Monitor available from Baker Hughes Incorporated, which is used to predict, diagnose, and monitor corrosion risk in refinery process equipment similar to Baker Hughes' Ionic Model. A critical input for these models is the MEA concentration in overhead water samples. The acquired data may be passed along to another device or person by a wired connection or a wireless connection. This would also allow for online monitoring of the industrial fluids from a remote site, which is different from the site of the industrial fluids.

The device may be portable in a non-limiting embodiment, and the device may be taken to the site of the industrial fluid, which reduces the amount of time between detecting the composition and relaying the results of such a detection. The device may rapidly detect the composition in another non-limiting embodiment, which may reduce the time to analyze the industrial fluids for compositions therein from days to minutes. For example, the time it takes to sample the industrial fluid and then detect the composition within the fluid may range from about 30 seconds independently to about 24 hours, alternatively from about 1 minute independently to about 5 hours, or from about 15 minutes independently to about 1 hour in another non-limiting example. As used herein with respect to a range, "independently" means that any lower threshold may be used together with any upper threshold to give a suitable alternative range.

Moreover, the device may be simple enough to allow non-technical users to sample industrial fluids for detecting compositions therein. This is contrasted to the previous need for highly trained laboratory professionals to perform such separation techniques and/or detection techniques for detecting compositions within a fluid. In one non-limiting embodiment, a chemical-specific cartridge may be used to introduce the composition into the device for detection of the composition. The device may be coupled with a computer, to provide laboratory-grade detection capabilities and automated advanced data processing at the site of the industrial fluid.

One non-limiting example of such a chemical-specific cartridge to be used with a detection device is the Monoethanolamine (MEA) Analysis cartridge, to be used with the OndaVia Basic Analysis System Model Number OV-PP-J003, both of which are supplied by OndaVia. This device utilizes surface-enhanced Raman spectroscopy as the detection technique where gold nanoparticles are embedded within the capillary or microchannel to enable trace level detection of a composition of interest. The device uses a Class III laser generating 60-mW of infrared light at 785 nm. The detection of compositions within the industrial fluid may be performed with an accuracy ranging from about 70% independently to about 99.5%, alternatively from about 90% independently to about 95%.

For the purposes of the present description, the term "industrial fluids" includes both gas and liquids. It also includes materials that may be solid at ambient temperatures but are fluid during an industrial process. Industrial fluids may be aqueous and non-aqueous fluids, including emulsions and other multiphase fluids, which are admixtures of aqueous and non-aqueous fluids and which may be present in the exploration for or production of oil and gas, during the refining of crude oil, during the production of chemical products, and combinations thereof. Industrial fluids may be or include, but are not limited to, cooling water, process water, drilling fluids, completion fluids, production fluids, crude oil, feed streams to desalting units, outflow from desalting units, refinery heat transfer fluids, gas scrubber fluids, refinery unit feed streams, refinery intermediate streams, finished product streams, and combinations thereof. A finished product may be a material that the refinery intends to sell or that does not require further refining, such as but not limited to diesel fuel, gasoline, and the like.

Scrubber fluids may interact with a second fluid to target undesirable compounds from the second fluid for subsequent removal or measurement of the targeted compound. A refinery fluid or feed is defined as any industrial fluid where the industrial fluid is further refined, i.e. additives may be added to the refinery fluid or compounds may be removed from the refinery fluid. Refinery fluids are typically associated with refining oil and/or gas fluids; however, fluids stemming from a chemical plant may also be considered a refinery fluid for purposes of the methods described.

For example, the water stream from a refinery feed may be sampled and introduced into the detection device to identify compositions therein, or water produced from a wellbore, etc. Other non-limiting examples of the types of industrial fluids may be or include, but are not limited to desalter wash water, influent and/or effluent from the desalter; water from an accumulator of a distillation tower overhead system; and the like. The sample may be collected from the industrial fluid in an amount ranging from about 200 mL independently to about 1000 mL, alternatively from about 10 mL independently to about 120 mL.

In employing one of the analytical techniques, samples may be introduced directly into the detection device from the industrial fluid. Any detection method known to those of ordinary skill in the art to be useful for this application may be employed with the process described herein. Alternatively, the sample may be conditioned by a method, such as but not limited to filtration, pH adjustment, chemical labeling, a separation technique, solid-phase extraction, adding background electrolyte (BGE) to the sample, adding a complexing agent to the sample, adding peroxide to the sample, adding a chelant to the sample, applying chelating resins to the sample, and combinations thereof prior to detecting at least one composition within the industrial fluid, prior to a separations technique, or both. A sample that has been conditioned is compositionally distinct from a sample that has not been conditioned. Examples of how the sample may be conditioned, such that the composition is compositionally distinct, are further described below.

'Chemical labeling' is defined herein to mean that a chemical reactant may react with the composition in the industrial fluid to produce a chemical label on the composition. The chemical label on the composition makes it easier to detect and/or quantify the amount of the composition present in the industrial fluid.

Particulate matter may be removed from the sample by filtration prior to introducing the sample into the detection device. In one non-limiting embodiment, the pH may need to be basic, such as from about 8 independently to about 14, or about 13 in another non-limiting embodiment. Any pH adjustment will depend on the chemistry and response of the analyte. Some analytes may require a low pH to improve separation, neutral pH to increase interaction with nanoparticles, etc. Sodium hydroxide, or a similar basic compound, may be used to adjust the pH to a desired amount. The adjustment of the pH may be beneficial in circumstances where hydrogen sulfide is a source of concern, and adjusting the pH may convert the $H_2S$ to a less active form. Alternatively, the sample may be treated with a metal oxide or hydrogen peroxide to remove or convert $H_2S$ to a non-interfering form. The sample may also be conditioned by adding a surfactant and/or a background electrolyte to the sample.

For example, an industrial fluid may be treated with a pre-concentrator to increase the relative concentration of an analyte of interest. In another embodiment, an industrial fluid may be subjected to an extraction process. In still another embodiment, the industrial fluids may be subjected to heat prior to being introduced into the detection device.

The sample, which may be a conditioned sample or an unconditioned sample, may be introduced into the device employing a detection technique, such as, but not limited to, surface enhanced Raman scattering (SERS), mass spectrometry (MS), nuclear magnetic resonance (NMR), ultraviolet light (UV) spectroscopy, UV spectrophotometry, indirect UV spectroscopy, contactless conductivity, laser induced fluorescence, and combinations thereof. The desired type of detection varies depending on the type of compositions analyzed. The amount of the sample introduced into the device ranges from about 3 μL to about 250 μL, alternatively from about 1 μL independently to about 50 μL.

A single composition or multiple compositions may be detected. Once a particular composition has been detected or identified, the amount of the composition may also be quantified. The composition may be detected within the fluid in an amount as low as 10 parts per billion (ppb), alternatively from about 10 ppb independently to about 10 ppm, alternatively from about 0.2 parts per million (ppm) independently to about 150 ppm, or from about 1 ppm independently to about 1000 ppm in another non-limiting embodiment.

The detected composition may be or include, but is not limited to, amines, sulfides, chlorides (organic and inorganic), bromides, organic acids, perchlorates, selenates, phosphates, polyphosphates, cyanide, selenium, borate, sulfides, mercaptans, primary amines, secondary amines, and tertiary amines, such as methylamine (MA), ethanolamine (MEA), dimethylethanolamine (DMEA), ammonia, mercaptoethanol, thioglycolic acid, glycols, polyols, polydimethylsiloxanes, organic halides, $C_1$-$C_{22}$ organic acids, hydroxyacids, imidazoline, alkyl pyridine quaternary compounds, imides, amides, thiophosphate esters, phosphate esters, polyamines, dimethyl fatty amines, quaternized dimethyl fatty amines, ethylene vinylacetate, phenylenediamine (PDA), hindered phenols, nitrites, sulfites, N,N'-diethyl hydroxylamine, hydrazine, ascorbic acid, organic nitroxides, triazoles and polytriazoles, hydroxylamines, acrylic acids and sulfonic acids, fatty acid methyl ester (FAME), propargyl alcohols, acetylenic alcohols, pyroles, indoles, indenes, thiophenols, dyes, $H_2S$, MEA triazine, MEA thiadiazine, MEA dithiazine, MA triazine, MA thiadiazine, MA dithiazine, metal ions, polynuclear aromatic hydrocarbons, BTEX solvents (benzene, toluene, xylene, and/or ethylbenzene), and combinations thereof. A single analyte or multi-analyte may be detected.

The metal ions may be or include, but are not limited to, iron, calcium, nickel, chromium, vanadium, copper, and the like. The polynuclear aromatic hydrocarbons may be or include, but are not limited to, asphaltenes, coke, coke precursors, naphthalene, perylene, coronene, chrysene, anthracene, and combinations thereof.

The presence of mercaptoethanol, thioglycolic acid, and 2-mercaptoethylsulfide may be used as an indicator that a corrosion inhibitor is present in a product or refinery intermediate fluid. Glycols, polyols, polydimethylsiloxanes may indicate the presence of antifoam additives in process fluids. Antifoamers and defoamers are added to industrial fluids (e.g. drilling fluids, completion fluids, etc.) to reduce or prevent foam from forming within the fluid. Organic halides, especially $C_1$-$C_{10}$ chlorinated solvents may indicate the presence of paraffin control additives, cleaners/degreasers in crude oil, etc.

$C_1$-$C_{22}$ organic acids may indicate the presence of lubricity additives in fuels. Hydroxyacids may be used for determining the presence of contaminant removal chemicals in refinery fluids. The presence of imidazoline, alkyl pyridine quaternary compounds, imides, amides, thiophosphate esters, phosphate esters, polyamines, dimethyl fatty amines, and quaternized dimethyl fatty amines may be used to monitor corrosion inhibitors in production fluids or refinery fluids. Ethylene vinylacetate may be used to monitor for the presence of cold flow additives in fuels.

Petrochemical industrial fluids may be monitored for the presence of compounds such as phenylenediamine (PDA), hindered phenols, and organic nitroxides. Oxygen scavengers, such as hydroxylamines, nitrites, sulfites, N,N'-diethyl hydroxylamine, hydrazine, and ascorbic acid may also be of interest in such fluids and may be monitored using the process described herein. NOx/SOx compounds (e.g. nitrite/nitrate, sulfite/sulfate, and the like) may be of interest in industrial fluids where such compounds may be discharged to the environment. The device may be used to determine the presence of spent/available organic nitroxides in petrochemical fluids for monitoring stability additives.

In one embodiment, the method described herein may monitor triazoles and polytriazoles in wastewater. The concentration of biocides in wastewater may also be determined, as well as phosphates and phosphonates. Other additives that may be in wastewater and may be monitored are within the scope of the methods and fluid compositions described herein.

In yet another embodiment, boiler water may be monitored for the presence of hydroxylamines. Cooling water may be monitored for an indication of scale inhibitors. Cooling water systems, e.g. the effluent from cooling towers, may be monitored for the presence of volatile organic compounds both for the purposes of environmental monitoring and as a method of determining the occurrence of leaks.

In another non-limiting embodiment, the method may be employed in specific process streams. In one such embodiment, the presence or absence of very low levels of contaminants in alkylation units may be determined. Organic acids, which are very corrosive compounds, that may be overhead in a distillation unit may also be determined and/or monitored.

A device may determine the concentration of an analyte of interest and then use the data to prepare a predictive model. For example, ethanolamine may be monitored in a fluid to predict whether that fluid, when passed through a heat exchanger or overhead line, will lead to conditions where a salt (for example, ethanolamine hydrochloride) will form and cause fouling and corrosion.

Parameters related to the industrial fluid may be altered based on the results or data obtained related to the identified composition(s) and the respective amount of the identified composition(s) within the industrial fluid. Such parameters may be or include, but not limited to, temperature, amount of the composition therein, pressure, and combinations thereof. In one non-limiting example, the temperature of a process may be altered in order to avoid the formation or deposition of solid amine hydrochloride salts within the process equipment if the concentration of a particular amine is determined to be above a pre-determined threshold value. In another non-limiting embodiment, the amount of specific amines or inorganic ions (such as chlorides) may be used to optimize process parameters of the desalter.

The parameter may be altered upstream or downstream of the location of the analyzed sample. For example, contaminant removal technology may be applied at the desalter (upstream) based on the quantitation of MEA in a water sample from the overhead system of the atmospheric distillation tower (downstream). Another non-limiting example includes quantitation of MEA in a water sample extract of desalted crude oil (upstream) where the data may be used to alter tower top temperature of atmospheric distillation tower (downstream).

In one non-limiting embodiment, the output may be employed directly to control an element of the process. For example, an undesirable composition may be monitored and a valve or pump operated to either speed up or slow down a specific process stream in response to the concentration of the undesirable composition. In another example, the input is used to change the pH of a process stream. The dosage of additives, such as but not limited to, corrosion inhibitors, hydrate inhibitors, anti-fouling agents, antifoaming agents, anti-scaling agents, demulsifiers, and the like may be optimized.

In another non-limiting embodiment, a device may be used with a Baker Hughes SENTRY SYSTEM™ to control the flow of additives to an oil well, such as the flow of corrosion inhibitors (e.g. hydrogen sulfide scavengers). In a refinery, other additives, such as a defoamer, may be employed. Any additive known to be useful in an industrial fluid to those of ordinary skill in the art may be optimized by the method described herein.

In another non-restrictive embodiment, the data obtained from a detective device may be inputted into a computer model, which may be particularly valuable in complex refining and chemical production units. In such applications, there may be many inputs, which when computed by the model, may change a number of process variables. For example, an increase in the targeted composition within the industrial fluid may require a change to a single flow of a single stream and to several other feed stream rates, and/or an increase in temperature and or pressures. In some non-limiting embodiments, the input may be from an analytical device present within a refinery, which may be used to change parameters of production units upstream and/or downstream from the location where the measurement was actually taken.

In some non-limiting instances, a separation technique may be performed on the sample prior to introducing the sample into the detection device. The separation technique may be performed at a remote location from the industrial fluid, or the separation technique may be performed at the site of the industrial fluid. Similarly, the detection technique may be performed at a remote location or at the site of the industrial fluid. The separation technique does not have to be performed by the same device as the detection technique, or even at the same location as the detection technique. However, a device may couple at least one separation technique with at least one detection technique for enhanced portability and efficiency of the device in a synergistic manner.

The desired type of separations technique applied to the sample depends on the type of industrial fluid, the desired composition to be detected, etc. Types of separation techniques include, but are not limited to, gas chromatography (GC), ion chromatography (IC), high performance liquid chromatography (HPLC), capillary electrochromatography (CEC); electrokinetic chromatography (EKC), such as capillary electrokinetic chromatography (CEC), micellar electrokinetic capillary chromatography (MECC), micellar electrokinetic chromatography (MEKC), ion exchange electrokinetic chromatography (IEEC); and electrophoretic methods, such as affinity capillary electrophoresis (ACE), non-aqueous capillary electrophoresis (NACE), capillary electrophoresis (CE), capillary zone electrophoresis (CZE), gradient elution moving boundary electrophoresis (GEMBE), capillary isotachophoresis (CITP), capillary isoelectric focusing (CIEF), and combinations thereof.

Non-limiting embodiments of the method may be or include a pass-through method, a retain and release method, and combinations thereof. Non-limiting examples of the pass-through method may be a mixed mode pass-through method, and a single mode pass-through method. The pass-through methods may utilize a solid phase extraction (SPE) sorbent to act as a filter and remove an interfering species, while leaving the target analyte in solution. The 'target analyte' is the compound of interest to be detected. The 'interfering species is any other compound that may be in the solution but is not the compound of interest to be detected, i.e. the interfering species may interfere with the detection of the compound of interest. A single mode sorbent may strongly attract ionic species, such as ion exchange interactions in a non-limiting embodiment. Mixed mode sorbents may have additional functions to interact with neutral molecules, polar molecules, non-polar molecules, and combinations thereof, such as hydrophilic/lipophilic (H/L) interactions in a non-limiting embodiment.

For a mixed mode pass-through method, a SPE cartridge with a mixed-mode anion exchange reversed-phase sorbent may be used in a non-limiting embodiment. The pH of the sample may be controlled as the sample contacts the sorbent, and the interfering species may interact with the positively charged ion exchange function of the solid phase sorbent, while the compound interest (e.g. amines) remain in the sample. At a pH of 12 (or at least 2 pH units above the compound of interest $pK_a$), the interfering species may be negatively charged, and the compound of interest may be uncharged (neutral). The anions (interfering species) may be strongly attracted to the positively charged anion exchange function of the sorbent, while the free compound of interest (e.g. uncharged amines) may pass through the sorbent. Because the sorbent has H/L interactions in addition to ion exchange, the amines of interest may also interact with the non-ionic portion of the sorbent. In a non-limiting embodiment, the amines of interest may be polar hydrophilic molecules and may form hydrogen bonds and may not strongly interact with the lipophilic portion of the sorbent. However, the amines may have an attraction to the polar hydrophilic function of the sorbent. In order to reduce these H/L interactions, a small amount (2-25 vol %) of methanol (MeOH) may be added to the sample. The MeOH may disrupt hydrogen bonding between the amines and the hydrophilic portion of the sorbent.

A non-limiting example of the mixed mode pass-through (MMPT) sample prep procedure may be as follows:
1. Pass 6-10 mL of a sample through 0.45 micron PP syringe filter to remove particulate and/or hydrocarbon contaminants.
2. Add 5 vol % MeOH to the sample.
3. Adjust the sample pH to about 12 with sodium hydroxide.
4. Pass the sample (pH 12) solution through the SPE cartridge. The sample volume may have a correction factor for hold-up volume and MeOH. (Hold-up volume refers to the volume of liquid that remains held-up in the sorbent after a given volume of liquid has been passed through.)
5. Pass 3 mL of sample through the SPE cartridge.

For a single mode pass-through (SMPT) for amine detection, the SPE sorbent may function as an anion exchange material that is positively charged and is independent of the functional pH range of the sorbent. In this mode, the H/L interactions are not applicable, which eliminates the need for an addition of MeOH. However, if interfering species are retained having H/L interactions, such species will not be removed from the sample with a SMPT method.

A non-limiting example of the SMPT sample prep procedure may be as follows:
1. Pass a 6-10 mL sample through a 0.45 micron PP syringe filter to remove particulate and/or hydrocarbon contaminants.
2. Adjust the pH of the sample to be about 12 with sodium hydroxide.
3. Pass about 2 mL of the sample solution (pH 12) through the SPE cartridge.
4. Pass about 3 mL* of the sample through the SPE cartridge. The sample volume may have a correction factor for hold-up volume and MeOH.

To summarize, the MMPT and SMPT methods employ anion exchange sorbents where the sample solution may retain interfering species at a high pH, while leaving the free amines in the sample for analysis.

The mixed mode retain and release (MMRR) mode may retain the target analytes on the sorbent, while the interfering species pass through. The target analytes may be released from the SPE sorbent by a subsequent solvent wash. The MMRR method may remove interferences and/or decrease the limit of detection for the analysis by concentrating the target analytes. The MMRR sample prep method may use a mixed mode cation exchange sorbent. Cation exchange sorbents have a negatively charged functional group incorporated on a polymer support. Adjusting the pH of the sample to at least about 2 pH units below the $pK_a$ of the target amine(s) may ensure that the compound of interest will be protonated (positively charged). The positively charged compound of interest (e.g. amines) may be retained by strong interaction with a negatively charged sorbent. At this pH, the interfering species may pass through the sorbent, since the interfering species may have either a neutral or a negative charge, so the interfering species may have little or no attraction to the sorbent. The compound of interest may be released by passing a high pH solution (e.g. $pH=pK_a+2$) through the sorbent.

A non-limiting example of the MMRR sample prep procedure may be as follows:
1. Pass 6-10 mL of sample through a 0.45 micron PP syringe filter to remove particulate and/or hydrocarbon contaminants.
2. Adjust the sample pH to about 6 with sulfuric acid ($H_2SO_4$).
3. Pass about 2 mL of the sample solution (pH 6) through a SPE cartridge.
4. Pass another 2 mL of the sample solution (pH 6) through the SPE cartridge.
5. Pass another 2 mL of the sample solution (pH 6) through the SPE cartridge.
6. Pass about 2 mL deionized (DI) water through the SPE cartridge.
7. Pass about 2 mL of the sample solution (pH 12 adjusted with sodium hydroxide) through SPE cartridge. The sample volume may have a correction factor for hold-up volume.

In summary, the MMRR method may employ a cation exchange sorbent to retain the target compound(s) at a low pH, while any interfering species pass through. The target compounds, such as amine(s) in a non-limiting embodiment may then be released from the sorbent at a high pH to be analyzed and/or detected.

The invention will be further described with respect to the following Example, which is not meant to limit the invention, but rather to further illustrate the various embodiments.

EXAMPLE 1

A known quantity of MEA was measured and added into the sample, which had a base fluid of DI water. The instrument was designed to detect MEA, so the instrument did not detect the other compounds that were also included in the sample. The other compounds were included in the sample to test whether the presence of multiple amines in the sample would affect the accurate determination of MEA.

The concentrations, known and detected, are measured in milligrams/liter (mg/L). Each sample also had also known compounds therein to determine the effect such compounds may have on the effect of detecting the MEA. Sample 1 had methylamine (MA) in an amount of 10 mg/L. Sample 2 had no other known compounds. Sample 3 had MA (20 mg/L), ethylamine (EA) (15 mg/L), methyl diethanolamine (MDEA) (20 mg/L), diglycolamine (DGA) (24 mg/L), and propylamine (PA) (20 mg/L). Sample 4 had MA in an amount of 75 mg/L. Sample 5 had acetic acid in an amount of 70 mg/L. Sample 6 and Sample 7 had no other known compounds.

As noted by TABLE 1, the acetic acid in sample 5 did not affect the measurement of MEA. Also noted by TABLE 1, it appears that MEA concentrations may be accurately measured, even in the presence of other compounds.

TABLE 1

Detected concentrations of MEA compared to known concentrations

| Sample | MEA Known Conc. | MEA Detected Conc. |
|---|---|---|
| 1 | 10 | 8 |
| 2 | 10 | 9, 11 |
| 3 | 21 | 24, 25 |
| 4 | 25 | 22, 24 |
| 5 | 30 | 29 |
| 6 | 50 | 57, 47 |
| 7 | 75 | 76 |

In the foregoing specification, the invention has been described with reference to specific embodiments thereof, and has been described as effective in providing methods and compositions for monitoring at least one industrial fluid at the site of the industrial fluid. However, it will be evident that various modifications and changes can be made thereto without departing from the broader spirit or scope of the invention as set forth in the appended claims. Accordingly, the specification is to be regarded in an illustrative rather than a restrictive sense. For example, specific industrial fluids, separation techniques, detection techniques, and compositions falling within the claimed parameters, but not specifically identified or tried in a particular composition or method, are expected to be within the scope of this invention.

The present invention may suitably comprise, consist or consist essentially of the elements disclosed and may be practiced in the absence of an element not disclosed. For instance, the method for monitoring at least one industrial fluid may consist of or consist essentially of introducing the sample into a device employing a detection technique, such as surface enhanced Raman scattering (SERS), mass spectrometry (MS), nuclear magnetic resonance (NMR), ultraviolet light (UV) spectroscopy, UV spectrophotometry, indirect UV spectroscopy, contactless conductivity, laser induced fluorescence, and combinations thereof and detecting at least one composition in the sample; where the industrial fluid is selected from the group consisting of a refinery fluid, a production fluid, cooling water, process water, drilling fluids, completion fluids, production fluids, crude oil, feed streams to desalting units, outflow from desalting units, refinery heat transfer fluids, gas scrubber fluids, refinery unit feed streams, refinery intermediate streams, finished product streams, and combinations thereof; the method may occur in an amount of time that is less than about 24 hours.

The fluid composition may consist of or consist essentially of a conditioned sample of an industrial fluid prepared for analysis by a device employing a detection technique selected from the group consisting of surface enhanced Raman scattering (SERS), mass spectrometry (MS), nuclear magnetic resonance (NMR), ultraviolet light (UV) spectroscopy, UV spectrophotometry, indirect UV spectroscopy, contactless conductivity, laser induced fluorescence, and combinations thereof; where the industrial fluid is selected from the group consisting of a refinery fluid, a production fluid, cooling water, process water, drilling fluids, completion fluids, production fluids, crude oil, feed streams to desalting units, outflow from desalting units, refinery heat transfer fluids, gas scrubber fluids, refinery unit feed streams, refinery intermediate streams, finished product streams, and combinations thereof; and where the conditioned sample is compositionally distinct as compared to a non-conditioned sample of the industrial fluid.

The words "comprising" and "comprises" as used throughout the claims, are to be interpreted to mean "including but not limited to" and "includes but not limited to", respectively.

What is claimed is:

1. A method for monitoring at least one industrial fluid comprising:
    a. introducing a sample of the at least one industrial fluid into a device employing a detection technique selected from the group consisting of surface enhanced Raman scattering (SERS), indirect UV spectroscopy, contactless conductivity, and combinations thereof; wherein the industrial fluid is selected from the group consisting of a refinery fluid, a production fluid, cooling water, process water, drilling fluids, completion fluids, production fluids, crude oil, feed streams to desalting units, outflow from desalting units, refinery heat transfer fluids, gas scrubber fluids, refinery unit feed streams, refinery intermediate streams, finished product streams, and combinations thereof; and
    b. detecting at least one composition within the sample of the at least one industrial fluid, wherein the at least one composition is monoethanolamine (MEA) in the presence of other compounds; and
    wherein the method occurs in an amount of time less than about 24 hours.

2. The method of claim 1, further comprising conditioning the sample prior to introducing the sample of the at least one industrial fluid into the device, wherein the conditioning is a method selected from the group consisting of filtration, pH adjustment, chemical labeling, a separation technique, solid-phase extraction, adding a background electrolyte (BGE) to the sample, adding a complexing agent to the sample, adding peroxide to the sample, adding a chelant to the sample, applying chelating resins to the sample, and combinations thereof.

3. The method of claim 2, wherein the conditioning is a separation technique selected from the group consisting of ion chromatography (IC), high performance liquid chromatography (HPLC), capillary electrochromatography (CEC); electrokinetic chromatography (EKC), affinity capillary electrophoresis (ACE), non-aqueous capillary electrophoresis (NACE), capillary electrophoresis (CE), capillary zone electrophoresis (CZE), gradient elution moving boundary electrophoresis (GEMBE), capillary isotachophoresis (CITP), capillary isoelectric focusing (CIEF), and combinations thereof.

4. The method of claim 1, wherein the at least one composition within the at least one industrial fluid is quantified in an amount greater than about 10 ppb.

5. The method of claim 1 further comprising altering or controlling at least one element of a process after detecting the at least one composition.

6. The method of claim 1, wherein the amount of the sample introduced into the device ranges from about 1 µL to about 250 µL.

7. The method of claim 1, wherein the detecting the at least one composition occurs in an amount of time ranging from about 30 seconds to about 5 hours.

8. A method for monitoring at least one industrial fluid comprising:
   a. performing a separation technique on a sample of the at least one industrial fluid to form a separated sample; wherein the separation technique is selected from the group consisting of ion chromatography (IC), high performance liquid chromatography (HPLC), capillary electrochromatography (CEC), electrokinetic chromatography (EKC), affinity capillary electrophoresis (ACE), non-aqueous capillary electrophoresis (NACE), capillary electrophoresis (CE), capillary zone electrophoresis (CZE), gradient elution moving boundary electrophoresis (GEMBE), capillary isotachophoresis (CITP), capillary isoelectric focusing (CIEF), and combinations thereof;
   b. introducing the separated sample into a device employing a detection technique selected from the group consisting of surface enhanced Raman scattering (SERS), nuclear magnetic resonance (NMR), indirect UV spectroscopy, contactless conductivity, and combinations thereof; and wherein the industrial fluid is selected from the group consisting of a refinery fluid, a production fluid, cooling water, process water, drilling fluids, completion fluids, production fluids, crude oil, feed streams to desalting units, outflow from desalting units, refinery heat transfer fluids, gas scrubber fluids, refinery unit feed streams, refinery intermediate streams, finished product streams, and combinations thereof;
   c. detecting at least one composition within the sample, wherein the at least one composition is monoethanolamine (MEA) in the presence of other compounds; and
   wherein the method occurs in an amount of time less than about 24 hours.

9. The method of claim 8, wherein the sample is conditioned prior to a step selected from the group consisting of performing the separation technique, introducing the sample into the device, and prior to both.

10. The method of claim 9, wherein the sample is conditioned by a method selected from the group consisting of filtration, pH adjustment, chemical labeling, solid-phase extraction, adding background electrolyte (BGE) to the sample, adding a complexing agent to the sample, adding peroxide to the sample, adding a chelant to the sample, applying chelating resins to the sample, and combinations thereof.

11. The method of claim 8, wherein the at least one composition within the at least one industrial fluid is quantified in an amount greater than about 10 ppb.

12. The method of claim 8, wherein the amount of the sample introduced into the device ranges from about 1 µL to about 250 µL.

13. The method of claim 8 further comprising altering or controlling at least one element of a process after detecting the at least one composition.

14. The method of claim 8, wherein the industrial fluid is selected from the group consisting of an aqueous fluid, a non-aqueous fluid, and combinations thereof.

15. The method of claim 8, wherein the detecting the at least one composition occurs in an amount of time ranging from about 30 seconds to about 5 hours.

16. A method for monitoring at least one industrial fluid comprising:
   a. conditioning a sample of the at least one industrial fluid by capillary electrophoresis (CE) prior to:
   b. introducing the sample into a device employing the detection technique of surface enhanced Raman scattering (SERS) or nuclear magnetic resonance (NMR); wherein the industrial fluid is selected from the group consisting of a refinery fluid, a production fluid, cooling water, process water, drilling fluids, completion fluids, production fluids, crude oil, feed streams to desalting units, outflow from desalting units, refinery heat transfer fluids, gas scrubber fluids, refinery unit feed streams, refinery intermediate streams, finished product streams, and combinations thereof; and
   c. detecting at least one composition within the sample of the at least one industrial fluid, wherein the at least one composition is monoethanolamine (MEA) in the presence of other compounds; and
   wherein the method occurs in an amount of time less than about 24 hours.

* * * * *